US006911818B2

(12) United States Patent
Julius

(10) Patent No.: US 6,911,818 B2
(45) Date of Patent: Jun. 28, 2005

(54) METHOD AND APPARATUS FOR EVALUATING MEASURING SIGNALS

(75) Inventor: Edmund Julius, Aachen (DE)

(73) Assignee: AMEPA Angewandte Messtechnik und Prozessautomatisierung GmbH, Aachen (DE)

(*) Notice: Subject to any disclaimer, the term of this patent is extended or adjusted under 35 U.S.C. 154(b) by 37 days.

(21) Appl. No.: 10/627,189

(22) Filed: Jul. 24, 2003

(65) Prior Publication Data
US 2004/0169502 A1 Sep. 2, 2004

(30) Foreign Application Priority Data
Jul. 25, 2002 (EP) .......................................... 02 016 627

(51) Int. Cl.⁷ ............................................. G01N 27/74
(52) U.S. Cl. ..................................................... 324/204
(58) Field of Search ........................ 324/232, 234–235, 324/239, 204; 73/DIG. 5; 222/591, 560, 603

(56) References Cited

U.S. PATENT DOCUMENTS

| 4,112,759 A | * | 9/1978 | Mizuno et al. ................ 73/295 |
| 4,816,758 A | | 3/1989 | Theissen et al. |
| 4,887,798 A | | 12/1989 | Julius |
| 5,042,700 A | * | 8/1991 | Ardell et al. ................ 222/590 |

FOREIGN PATENT DOCUMENTS

| DE | 3142681 | 5/1983 |
| DE | 3439369 | 4/1986 |
| DE | 3722795 | 1/1989 |

* cited by examiner

Primary Examiner—Bot LeDynh
(74) Attorney, Agent, or Firm—W. F. Fasse; W. G. Fasse

(57) ABSTRACT

A method for evaluating measuring signals of an electromagnetic field is disclosed which is in interaction with an electrically conductive fluid for detecting components in the fluid which differ from the electric conductivity of the fluid, with the measuring signals being divided into at least two channels and being evaluated in order to detect different distributions and concentrations in the fluid.

17 Claims, 3 Drawing Sheets

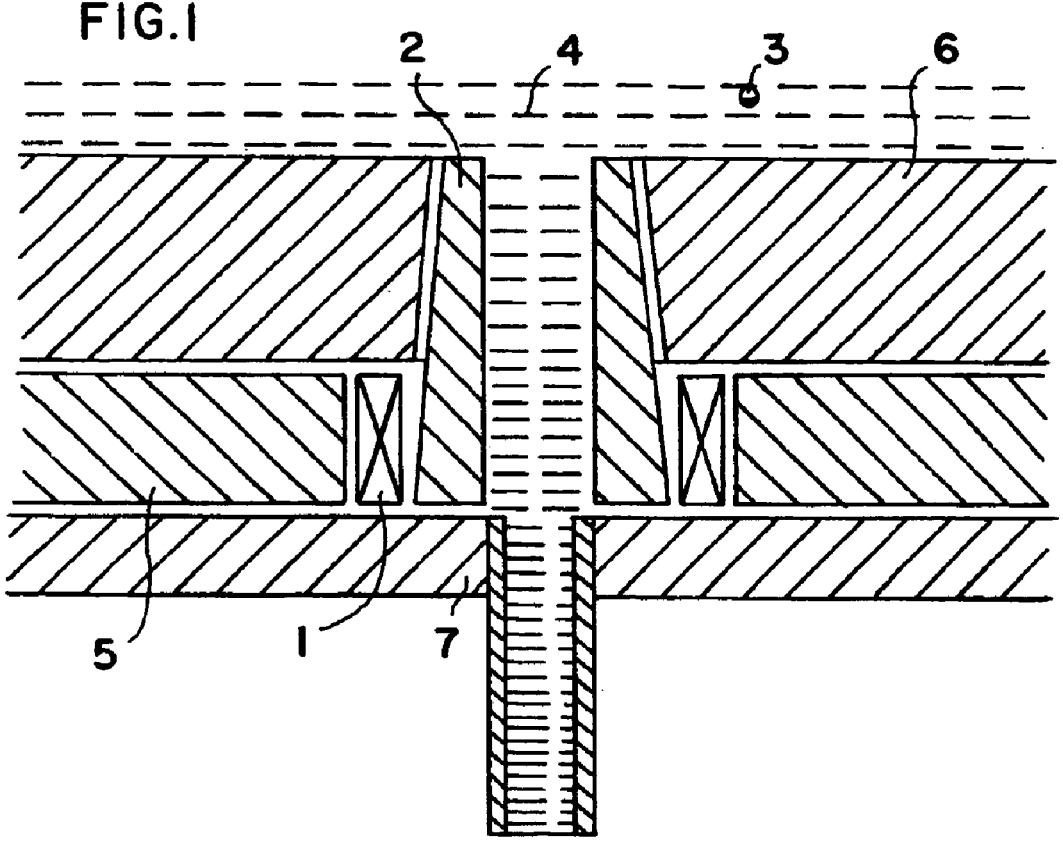
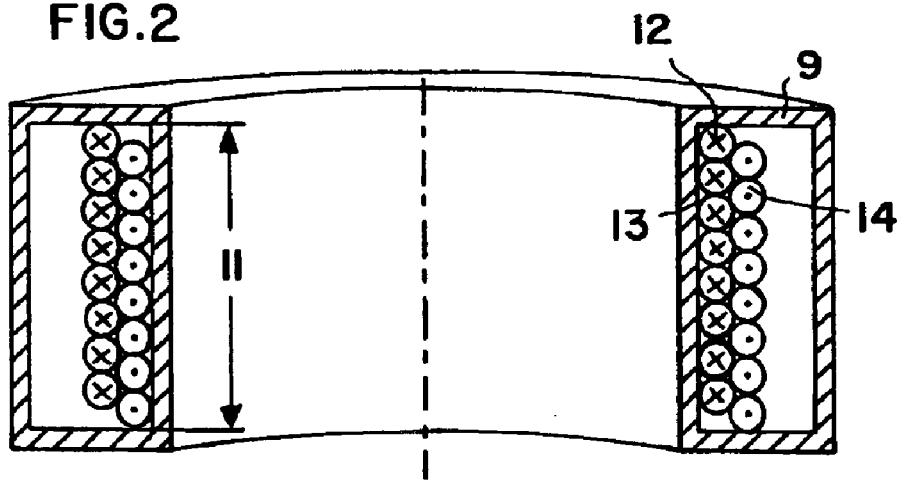

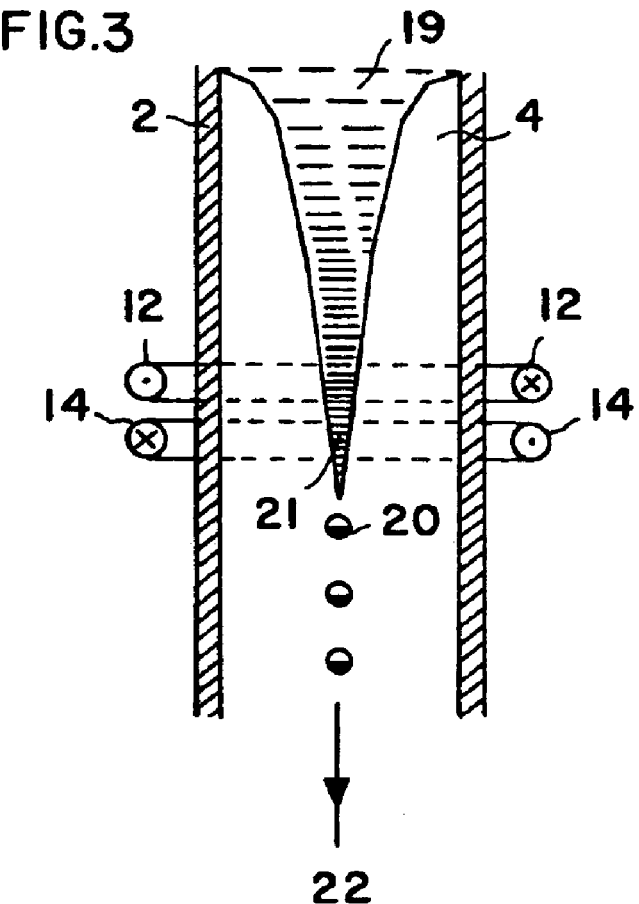
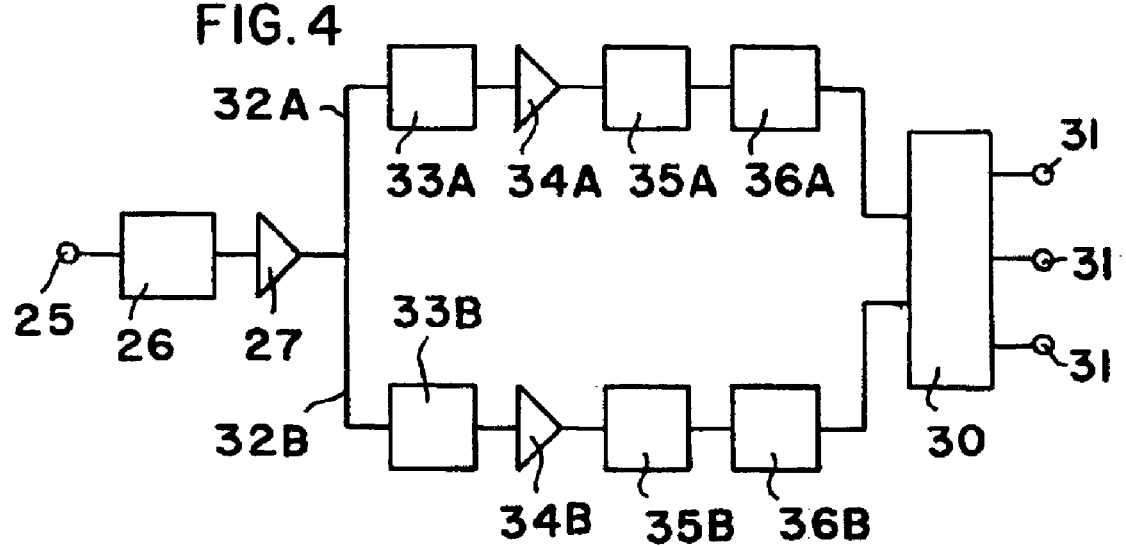

METHOD AND APPARATUS FOR EVALUATING MEASURING SIGNALS

FIELD OF THE INVENTION

The invention relates to a method for evaluating measuring signals of an electromagnetic field which is in interaction with an electrically conductive fluid for detecting components in the fluid which differ with respect to the electric conductivity of the fluid, with the measuring signals being divided into at least two channels and being evaluated in order to detect different distributions and concentrations in the fluid.

BACKGROUND INFORMATION

The fluid can be an electrically conductive melt which flows through a channel from a metallurgical vessel. The components are then typically gases or slag. Coherent components shall be understood as being regions of components which expand especially in the direction of flow such as threads and whose extension in the direction of flow is typically much larger than the channel diameter. Discrete components shall be understood as incoherent regions of components or particles whose extension in the direction of motion is typically smaller than the channel diameter.

The invention similarly relates to a method in which the disturbance of an electromagnetic field which penetrates the flowing melt at least partly is evaluated at a measuring point which is flowed through by the melt and which is generated by at least one transmitter coil which is flowed through by alternating current. Generic apparatuses comprise in addition to the transmitter coil a measuring element for measuring disturbances of the field in the measuring point and an evaluating device by means of which non-metallic components such as gases or slag are detectable by means of a disturbance in the field.

When re-filling or pouring metal melt from a metallurgical vessel (e.g. a converter, kettle or header), it is desirable not to transfer slag (non-metallic phase components) swimming on the metal surface to the next vessel. The generic methods and apparatuses are used for monitoring the outflowing melt, so that measures can be taken during the detection of slag in order to suppress the transfer of slag. These measures can consist of the generation of a warning signal or the automatic termination of the re-filling process or taking an influence on the flow. Measures for influencing the flow are the reduction of the outflow cross section or the injection of gases for example, typically argon or nitrogen, into the outflow region in order to prevent the formation of eddies. The measuring point is typically arranged above a control member controlling the outflow.

In the generic methods and apparatuses an alternating magnetic field is established at a measuring point in the pouring channel by means of a transmitter coil which is flowed through by alternating current. This field produces a voltage in the flowing melt which on its part produces an eddy current in the electrically conductive melt. This current on its part produces an alternating magnetic field which can be measured with a measuring element.

If the outflowing melt contains components which show a lower electric conductivity than the metal, the current distribution in the melt changes and thus the field strength of the alternating magnetic field. By measuring the change of the magnetic field strength at the measuring point, entrained non-metallic components are detected. If the summarized change of the field strength reaches a threshold amplitude, a warning and/or control signal is triggered.

A generic method and a respective apparatus has been described in DE 31 42 681 A1. It has been proposed here to measure changes in the electromagnetic field at the measuring point by means of the voltage induced in a receiver coil, which like the transmitter coil is arranged concentrically about the pouring channel of a metallurgical vessel.

Improvements of this method are shown in DE 34 39 369 A1 and DE 37 22 795 A1. It is proposed on the one hand to charge the transmitter coil with different, mutually overlapping frequencies. A highly differentiated picture of the flowing melt is recognizable from the reaction in the receiver coil, so that already a very low share of slag can be detected in the same. It is proposed on the other hand to arrange the transmitter and receiver coils in a non-magnetic vessel in order to avoid the signal drift (i.e. the distortion of the magnetic field strength as measured at the measuring point) due to the temperature changes of the ferromagnetic floor plate of a metallurgical vessel.

It is also generally known to compensate the signal drift by measuring the coil temperature and correcting the measured values at least in part. If ferromagnetic metal parts are located close to the coils, the interconnection between temperature and drift of the measuring signals is non-linear, so that the influence of the temperature on the signals cannot be eliminated completely. Despite improvements already achieved, a residual quantity of slag is also regularly transferred to the next vessel with the known generic methods and apparatuses towards the end of the discharging process. Rising requirements placed on the degree of purity of the final product can therefore frequently not be fulfilled with the known methods and apparatuses.

The reason for this low residual quantity is on the one hand the technically caused detection limit of the employed generic apparatuses and on the other hand a process which is known as "continuous intermixing": Towards the end of the discharging process a so-called whirl sink can occur during the outflow of a liquid from a vessel. The slag "swimming" on the surface of the metallic melt as a result of its lower density is drawn into the pouring channel as a "thread" by such a whirl, whereby its cross section and thus the percentage by mass of the slag in the melt rises continuously from virtually zero. As long as the percentage by mass of the slag in the melt lies below the threshold amplitude of the generic apparatus, it will not be detected by the same and the slag will continue to flow along in an undetected fashion. The threshold amplitude of the generic apparatuses cannot be reduced at will because disturbance signals which are generally known in signal engineering as "noise" and especially temperature drifts will superpose the measuring signals. As a result of these unavoidable error sources a quasi "natural" detection limit is defined for the generic methods and apparatuses which cannot be undercut.

According to standing doctrine, the known process of "continuous intermixing" of slag during the occurrence of a whirl sink is characterized in that the slag is entrained from the start of the intermixing process in form of a "slag thread" whose cross section rises more or less continuously. In the spectral analysis of measured values of the known generic apparatuses pulse-like disturbances of the field were observed at the measuring point. The form of the pulses of these disturbances corresponds to that of discrete, electrically non-conductive concentrations in the melt which pass through the electromagnetic field of the transmitter coil.

As a result of a purposeful observation of these disturbances which according to standing doctrine are negligible as "noise" it was proven that the continuous sucking in of a thin thread frequently precedes the sucking in of smaller discrete quantities or that the thread is also interrupted several times.

SUMMARY OF THE INVENTION

The invention is based on the object of providing a method and an apparatus for evaluating measuring signals of an electromagnetic field which is in interaction with an electrically conductive fluid, for detecting components in the fluid which differ from the fluid with respect to electric conductivity, and especially for detecting entrained slag in a flowing metallic melt, with which it is possible to reduce considerably as compared with known methods and apparatuses the residual quantity of slag which is entrained towards the end of re-filling from a metallurgical vessel.

A method is to be proposed in particular with which it is possible to detect and evaluate simultaneously both very weak as well as very strong measuring signals which are obtained from an electromagnetic field which is in interaction with a flowing metallic melt containing non-metallic components and whose share in the melt can be very small and also very large and which can occur both discretely as well as in regions which are extended in the direction of movement.

On the other hand, the vessel can also run off without virtually any discharge eddies. In this case, the percentage by volume of the light matter rises virtually in a sudden manner. The object is therefore to propose methods and apparatuses with which non-metallic admixtures, and slag in particular, can be detected in an outflowing metal melt with a higher sensitivity. It is intended to detect not only smaller quantities of the admixtures, but in particular small discrete admixtures and the time of occurrence.

Based on generic methods and apparatuses the object of the invention on the basis of this finding is achieved in such a way that different concentrations and distributions of the components in the flowing melt as well as superimposed disturbance signals are separated on the basis of the time characteristics of the measured disturbances and are processed separately. Two time and frequency regions are distinguished in principle.

In order to reduce the influence of disturbances of the field by temperature changes in particular, entrained non-metallic components, and especially thread-like admixtures expanding in the direction of movement, are detected on the basis of disturbances of the field above a lower high-pass cut-off frequency $f_{Gu}$. The swirling in and growth of thread-like admixtures concerns a low process in the second to minute range. The thus caused disturbances to the field can be separated at least in part by a high-pass filter from the disturbances of the field by temperature changes. The two time ranges overlap and, as a result, it is not possible to clearly assign very small disturbances in the field to a time range.

Furthermore, non-metallic components which are distributed in the melt and are entrained discretely are detected on the basis of disturbances of the field above an upper high-pass cut-off frequency $f_{Go}$. Discretely entrained components produce pulse-like disturbances of the field whose width is lower by several powers of ten than disturbances caused by temperature changes and clearly smaller than disturbances caused by admixtures which are expanded in the direction of flow. The disturbances of the field caused by discretely entrained components can be separated nearly completely from the other disturbances by a second high-pass filter with a cut-off frequency $f_{Go}$ and can be amplified separately. As a result, concentrations of entrained non-metallic components can be detected which are below those of known apparatuses by more than one power of ten. In addition to the detection of minute concentrations of components, the time and the quantity of entrained discrete admixtures is an indication for the impending entrainment of larger quantities of non-metallic components. The knowledge about the quantity and the time of the entrained components allow an early initiation of flow-influencing measures, so that the entrained quantity of components is reduced drastically in comparison with current methods.

Especially advantageously, the signal characteristic of the second channel is subtracted from the signal characteristic of the first channel. The resulting differential signal can then be used in order to detect the direction of flow of expanded components in the melt.

When monitoring metallic melts during the outflow from metallurgical vessels, the product of cut-off frequency and flow speed at the measuring point of between 0.001 m/s² to 0.01 m/s² has proven to be advantageous for the lower high-pass cut-off frequency and between 0.1 m/s² to 10 m/s² for the upper high-pass cut-off frequency.

The evaluator of an apparatus in accordance with the invention is equipped for this purpose in a first channel with a respective high-pass filter element of the cut-off frequency $f_{Gu}$. This channel allows detecting the entrainment of non-metallic thread-like admixtures especially expanded in the direction of flow with a simultaneous reduction of the disturbances by temperature changes. In a second channel the evaluator is equipped with a high-pass filter element of the cut-off frequency $f_{Go}$. Discretely entrained components can be detected separately and can be further processed. The apparatus thus also allows the simultaneous proof of slag components which are expanded in the direction of flow and discretely entrained slag components and/or gas bubbles.

The invention separately detects and evaluates especially larger contingent distributions of the components and smaller, discretely occurring components in the fluid.

Receiver coils are preferably used as measuring elements in the methods and apparatuses in accordance with the invention in which an alternating magnetic field generated by a transmitter coil again induces an alternating voltage. Any disturbance of the field can then be measured as a disturbance of the alternating voltage induced into the receiver coil. Principally it is possible to use the transmitter coil simultaneously as a receiver coil because the inductive effect of the electromagnetic field is measurable in the same. In this way an apparatus in accordance with the invention can advantageously be configured in an especially compact way.

The voltage induced in the receiver coil is composed of two components. A voltage $U_o$ is induced in the receiver coil by the electromagnetic field of the transmitter coil. It is a function of the transmitter current, the frequency and the mutual inductivity between transmitter and receiver coil. A voltage is induced in the flowing melt by the electromagnetic field of the transmitter coil which is proportional to the transmitter current, frequency and the mutual inductivity between transmitter coil and melt. This voltage on its part produces eddy currents in the melt which on their part produce an electromagnetic field which induces in the receiver coil a voltage dU which is proportional to the magnitude of the eddy currents, the frequency and the mutual inductivity between melt and receiver coil. The measurement sensitivity of this apparatus encounters its limits where a change in voltage dU in the voltage $U_o$ is not clearly recognizable. The larger the ratio $dU/U_o$ the larger the measurement sensitivity of the apparatus.

In the detection of slag it may be appropriate to terminate the discharging process of the metallurgical vessel already at the lowest quantities of entrained slag. In this case it is sufficient when the evaluator only comprises one filter element with which discretely entrained components can be proven.

Depending on the quality requirements of the users of the apparatus, more or less non-metallic components can flow out with the melt. Preferably, the apparatus therefore comprises an element which sums up the detected measured values and thus produces a variable which is proportional to the quantity of the entrained components and which on exceeding a predetermined limit value supplies a signal for triggering a flow-influencing device, e.g. a locking device.

In the apparatus in accordance with the invention the transmitter coil and/or the receiver coil can preferably be flowed through by the melt. The windings of the respective transmitter coil are arranged at least partly around the flowing melt.

In a preferred embodiment, the transmitter and/or receiver coils are arranged in a metallic housing which at least partly is non-ferromagnetic. This housing is used as a support and protection of the coils against mechanical or thermal stresses. To ensure that electromagnetic fields can penetrate a section of the housing the same must consist of a non-ferromagnetic material.

Especially preferably, mutually assigned transmitter and receiver coils are arranged in a common metallic housing. The thus formed constructional unit made of transmitter and receiver coil thus especially facilitates the exchange as well as retrofitting. For this purpose the coils which are specifically adjusted to the respective task can be housed in the specially designed metallic housings which allow an easy exchange even in rough operating conditions found at the customer's plant. Moreover, the coils are protected against mechanical and thermal stress.

A further improvement of the measurement sensitivity of the apparatus can be achieved when the transmitter and receiver coil are axially spaced and are separated by a metallic wall from each other and either both coils are housed in a common housing or each coil is housed in a separate housing. The housing(s) consist(s) of a metallic material which is not ferromagnetic at least in sections. If the transmitter and receiver coil are situated close by, the mutual inductivity between them is high and, as a result, the voltage $U_o$. If the mutual inductivity can be reduced between transmitter and receiver coil without the mutual inductivity between transmitter coil and the melt and between melt and receiver coil being reduced to the same extent, the measurement sensitivity can be increased. This is achieved with the proposed apparatus. As a result of a distance between transmitter and receiver coil the mutual inductivity between the coils is reduced more clearly than the mutual inductivities between the coils and the flowing melt, so that the ratio $dU/U_o$ increases. This effect is further enhanced by the metallic separating wall between transmitter and receiver coil. The distance d should be smaller than the difference between the inner radius of the coil housing and the inner radius of the channel flowed through by the melt.

Transmitter and/or receiver coils of an apparatus in accordance with the invention can advantageously be integrated in a section of a pouring channel of a metallurgical vessel, which pouring channel mostly consists of a ceramic material. The measuring point and thus the place according to whose state a decision is made on the continuation of the pouring process, is then arranged especially close to the outlet of the metallurgical vessel.

The methods and apparatuses in accordance with the invention are especially suitable for the further evaluation of the signals determined in the measuring points, especially for classification in patterns for the statistical correlation with further information which can have an influence on the entrainment of impurities. Such information can be, for example, the current remaining content of the metallurgical vessel, the state with regard to wear and tear of the pouring channel or the age of the ceramic lining. Comparison values and estimates for future discharges or information concerning the initiation of warning or control signals during the recognition of typical patterns preceding the entrainment of impurities can be derived from preceding pouring processes.

BRIEF DESCRIPTION OF THE DRAWINGS

Embodiments are shown in the drawings for the purpose of explaining the invention. Similar elements in different embodiments are shown with the same reference numerals and different alphabetic letters, wherein:

FIG. 1 shows a longitudinal sectional view through the pouring channel of a pouring ladle with an apparatus in accordance with the invention;

FIG. 2 shows a first coil arrangement for an apparatus in accordance with the invention;

FIG. 3 shows an enlarged longitudinal sectional view through the pouring channel according to FIG. 1;

FIG. 4 shows a circuit diagram of the apparatus in accordance with the invention;

Figure 5:
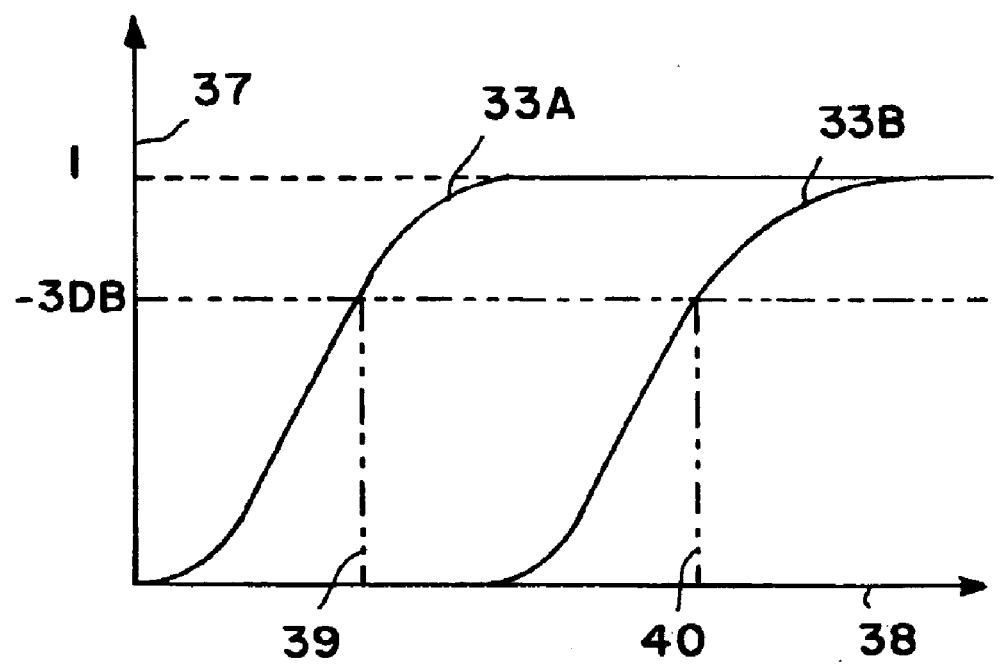
FIG. 5 shows the filter characteristics of the apparatus in accordance with the invention.

DETAILED DESCRIPTION OF PREFERRED EXAMPLE EMBODIMENTS AND OF THE BEST MODE OF THE INVENTION

FIG. 1 shows a coil arrangement 1 of an apparatus in accordance with the invention on the ceramic pouring channel 2 in the floor region 3 of a pouring ladle (not shown in closer detail) through which metallic melt flows out. The flow speed at the measuring point is close to 2 m/s.

The pouring ladle comprises a steel supporting construction 5 and a ceramic lining 6 in the floor region, which lining protects the steel supporting construction 5 from damage by the metallic melt 4. The ceramic pouring channel 2 penetrates the lining 6 and the supporting construction 5 and can be closed off below the supporting construction 5 by a parallel-seat gate valve 7 in a manner not shown in closer detail. The coil arrangement 1 is inserted in the supporting construction 5 between the lining 6 and the parallel-seat gate valve 7 around the pouring channel 2.

The coil arrangement shown separately in FIG. 2 is arranged in a toroidal fashion with a rectangular housing 9 stretched in the direction towards the torus axis. The toroidal housing 9 is adjusted according to the respective application to the components determining the outflow region of the metallurgical vessel such as the thickness of the supporting construction and/or the diameter of the ceramic pouring channel. The inner diameter of the housing lies close to 300 mm and the wall thickness of the austenitic housing close to 1 mm. A transmitter coil 12 and a receiver coil 14 are arranged within the housing 9 on its inner side 13 over its entire width 11. The number of windings of the coils is 25. The transmitter coil is connected with an A.C. generator (not shown here) which supplies the transmitter coil with an alternating current of 100 mA for example and a frequency of 100 Hz and the receiver coil is connected with the input of a demodulator 25.

FIG. 3 shows the function of the apparatus in accordance with the invention in a schematic view: The metallic melt 4 flows from the metallurgical vessel through the ceramic pouring channel 2. Towards the end of the pouring process, slag 19 is entrained increasingly into the pouring channel 2. As is shown, the slag 19 can be drawn in at first in discrete quantities 20 and later in a continuous thread 21 whose percentage by mass in the melt 4 rises continuously.

The transmitter coil 12 produces in the flowing metal melt 4 an alternating magnetic field according to the applied alternating voltage (not shown in closer detail), with the field lines of said alternating field extending in the melt 4 at the height of the transmitter coil in the direction of flow 22. The alternating magnetic field produces so-called eddy currents in the metallic melt which on their part produce a voltage (not shown in closer detail) in the receiver coil 24 which is tapped for detecting slag.

FIG. 4 shows the signal processing. The voltage from the receiver coil 14 is conducted to the input 25, demodulated in a measuring transducer 26 and conducted through an amplifier 27. The amplified signal is conducted in a first signal path 32*a* via a first filter 33*a* and amplified in an amplifier 34*a*, summed up in a summing element 35*a* and compared in an amplitude filter 36*a* with a limit amplitude (not shown). Both the signal as well as a second signal are supplied to the evaluating element 30 when the limit amplitude is exceeded. The amplified signal is conducted in a second signal path 32*b* via a second filter 33*b* and similarly amplified in an amplifier 34*b* and summed up in a summing element 35*b* and compared in an amplitude filter 36*b* with a limit amplitude (not shown). Both the signal as well as a second signal are supplied to the evaluating element 30 when the limit amplitude is exceeded, which evaluating element generates warning and control signals on the outputs 31.

The transmission characteristics 37 of the filters 33*a* and 33*b* are shown in FIG. 5 in a common diagram as a function of the frequency 38. The first filter 33*a* comprises a cut-off frequency 39 at 0.001 Hz. The second filter 33*b* has a cut-off frequency 40 at 5 Hz. The cut-off frequencies 39 and 40 designate the frequency values below which the respective input signal is dampened by more than 3 dB. The signal on the output of the first filter 33*a* is produced substantially by larger contiguous (thread-like) slag components. The signal on the output of the second filter 33*b* is produced by discretely entrained slag components.

Figure 6:
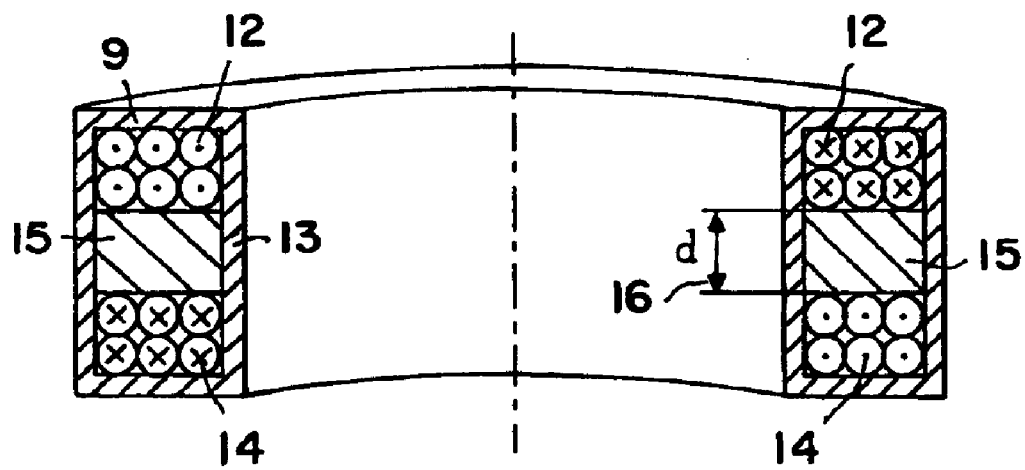
FIG. 6 shows a second coil arrangement for an apparatus in accordance with the invention.

FIG. 6 shows an alternative embodiment of the coil arrangement according to FIG. 2. In the housing 9 the transmitter coil 12 and the receiver coil 14 are housed at a distance 16 from each other and are separated by a metallic wall 15. The electromagnetic field of the transmitter coil at the location of the receiver coil is weaker as a result of the coils than in the case of coils which are situated adjacent to each other. It is reduced further by the damping effect of the metallic wall. The transmitter coil is connected with an a.c. generator (not shown) and the receiver coil with the input of the demodulator 25.

What we claim is:

1. A method for evaluating measuring signals of an electromagnetic field which is in interaction with an electrically conductive fluid for detecting components in the fluid which differ with respect to the electric conductivity of the fluid, characterized in that the measuring signals are divided into at least two channels and are evaluated in order to detect different distributions and concentrations in the fluid, characterized in that the electromagnetic field is generated by at least one transmitter coil flowed through by an alternating current, the fluid is a flowing metallic melt and is penetrated at least partly by the field at a measuring point flowed through by the melt and entrained non-metallic components are detected at the measuring point by means of disturbances in the field, with non-metallic components which are entrained in a contiguous fashion in a manner expanded in a direction of flow of the melt being detected in the melt on the basis of disturbances in the electromagnetic field in a first channel above a lower cut-off frequency $f_{Go}$ and simultaneously components distributed discretely in the melt being detected in the melt in a second channel above an upper cut-off frequency $f_{Go}$.

2. The method as claimed in claim 1, characterized in that the flowing metallic melt is a steel melt flowing from a metallurgical vessel and the non-metallic components are slag and/or gases.

3. The method as claimed in claim 1, characterized in that a product of the upper cut-off frequency $f_{Go}$ and a flow speed v of the flowing metallic melt is from 0.1 m/s$^2$ to 10 m/s$^2$ at the measuring point.

4. The method as claimed in claim 1, characterized in that a product of the lower cut-off frequency $f_{Gu}$ and a flow speed v of the flowing metallic melt is from 0.001 m/s$^2$ to 0.01 m/s$^2$ at the measuring point.

5. The method as claimed in claim 1, characterized in that the disturbances in the electromagnetic field generated by the at least one transmitter coil are detected on the basis of disturbances of the voltage induced in a receiver coil.

6. An apparatus for detecting non-metallic components in a flowing metallic melt with at least one transmitter coil which is flowed through by an alternating current for generating an electromagnetic field which penetrates the flowing melt at least partly, a measuring element for measuring disturbances of the field at a measuring point which is flowed through by the melt and with an evaluating device, characterized by a first filter element which guides the disturbances of the electromagnetic field above a lower cut-off frequency $f_{Gu}$ into a first channel with which non-metallic components can be detected which are entrained by the melt and are expanded especially in the direction of flow, and by a second filter element which guides the disturbances of the electromagnetic field above an upper cut-off frequency $f_{Go}$ into a second channel with which components can be detected which are distributed in the melt and are entrained in a discrete manner.

7. The apparatus as claimed in claim 6, characterized by a summing element in at least one channel, in which the measured values detected in the channel are summed up into a summary value and by an amplitude filter which triggers a signal when the summary value exceeds a limit amplitude.

8. The apparatus as claimed in claim 6, characterized in that the product of upper cut-off frequency $f_{Go}$ and a flow speed v is between 0.1 m/s$^2$ to 10 m/s$^2$ at the measuring point.

9. The apparatus as claimed in claim 6, characterized in that the product of lower cut-off frequency $f_{Gu}$ and the flow speed v is between 0.001 m/s$^2$ to 0.01 m/s$^2$ at the measuring point.

10. The apparatus as claimed in claim 6, characterized in that a measuring element is a receiver coil and that disturbances of the electromagnetic field at a measuring point can be detected on the basis of disturbances of the voltage induced in the receiver coil.

11. The apparatus as claimed in claim 6, characterized in that the transmitter coil can also be flowed through by the melt.

12. The apparatus as claimed in claim 6, characterized in that the transmitter coil is simultaneously the measuring element.

13. The apparatus as claimed in claim 10, characterized in that the transmitter and/or receiver coil are each individually arranged in a metallic housing which is at least partly non-ferromagnetic.

14. The apparatus as claimed in claim 10, characterized in that the transmitter and receiver coils are arranged in a common metallic housing which is at least partly non-ferromagnetic.

15. The apparatus as claimed in claim 10, characterized in that the transmitter and receiver coil are axially spaced from each other and are separated from each other by a metallic wall and either both coils are arranged in a common housing or each coil is housed in a separate housing, with the housing(s) consisting of a metallic material and the metallic material being non-ferromagnetic at least in sections.

16. The apparatus as claimed in claim 10, characterized in that the transmitter and receiver coils are integrated in at least one section of the pouring channel of a metallurgical vessel.

17. A method of using the apparatus as claimed in claim 6, for initiating a warning signal and/or a control signal for triggering a flow control device and/or a device for modifying the flow of the metallic melt when detecting discrete and/or contiguous impurities.

* * * * *